United States Patent [19]

Itaya et al.

[11] 4,083,855
[45] Apr. 11, 1978

[54] METHOD FOR PRODUCING A γ-LACTONE

[75] Inventors: Nobushige Itaya, Nishinomiya; Fumio Fujita, Ibaraki, both of Japan

[73] Assignee: Sumitomo Chemical Company, Limited, Osaka, Japan

[21] Appl. No.: 765,780

[22] Filed: Feb. 4, 1977

[30] Foreign Application Priority Data

Feb. 19, 1976 Japan .................................. 51/17580

[51] Int. Cl.² .......................................... C07D 307/32
[52] U.S. Cl. .............................. 260/343.6; 260/514 H; 560/124; 560/219
[58] Field of Search ...................................... 260/343.6

[56] References Cited

U.S. PATENT DOCUMENTS 3,488,732  1/1970  Heiba et al. ....................... 260/343.6

FOREIGN PATENT DOCUMENTS 2,233,244  1/1973  Germany ............................ 260/343.6

OTHER PUBLICATIONS

Bott, *Angew. Chem.*, 77 Jahrg. 1965, No. 21, p. 967.

*Primary Examiner*—Cecilia M. S. Jaisle
*Attorney, Agent, or Firm*—Stevens, Davis, Miller & Mosher

[57] ABSTRACT

A method for producing a 3,3-dimethyl-4-(2,2-dihalogenovinyl)-4-hydroxybutyric-1,4-lactone of the formula,

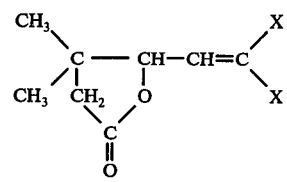

wherein X is a halogen atom, which comprises reacting a 1,1,1-trihalogeno-4-methyl-3-pentene-2-ol of the formula,

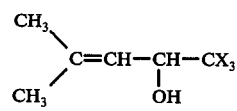

wherein X is a halogen atom, or a 1,1,1-trihalogeno-4-methyl-4-pentene-2-ol of the formula,

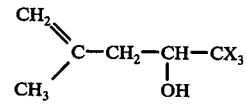

wherein X is a halogen atom, or the mixture of the both compounds with vinylidene chloride of the formula,

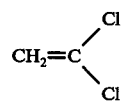

in sulfuric acid.

2 Claims, No Drawings

METHOD FOR PRODUCING A γ-LACTONE

The present invention relates to a method for producing a 3,3-dimethyl-4-(2,2-dihalogenovinyl)-4-hydroxybutyric-1,4-lactone of the formula (I),

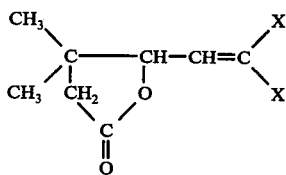

wherein X is a halogen atom.

The lactone of the formula (I) can be obtained by reacting a 1,1,1-trihalogeno-4-methyl-3-pentene-2-ol of the formula (II),

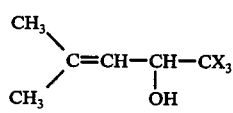

wherein X is a halogen atom, or a 1,1,1-trihalogeno-4-methyl-4-pentene-2-ol of the formula (II)',

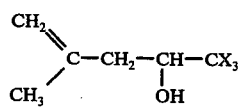

wherein X is a halogen atom, or the mixture of the both compounds with vinylidene chloride of the formula (III),

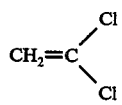

in sulfuric acid. In the process of the present invention, preferable example of the halogen atom is chlorine or bromine atom. This process is represented by the following reaction.

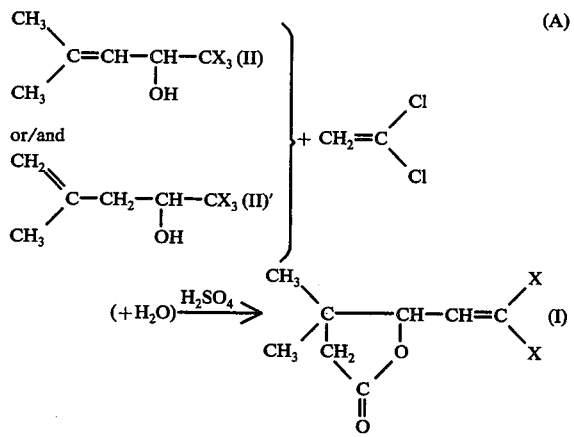

In this equation, X is a halogen atom.

The lactone (I) of the present invention is easily converted to 2,2-dimethyl-3-(2,2-dihalogenovinyl)cyclopropanecarboxylic acid (VI), for example, by the following reaction. The thus obtained cyclopropanecarboxylic acid is an acid moiety of the synthetic pyrethroid type compounds which attract attention as a useful insecticide [M. Elliott, et al., Nature, 246, 169 (1973)].

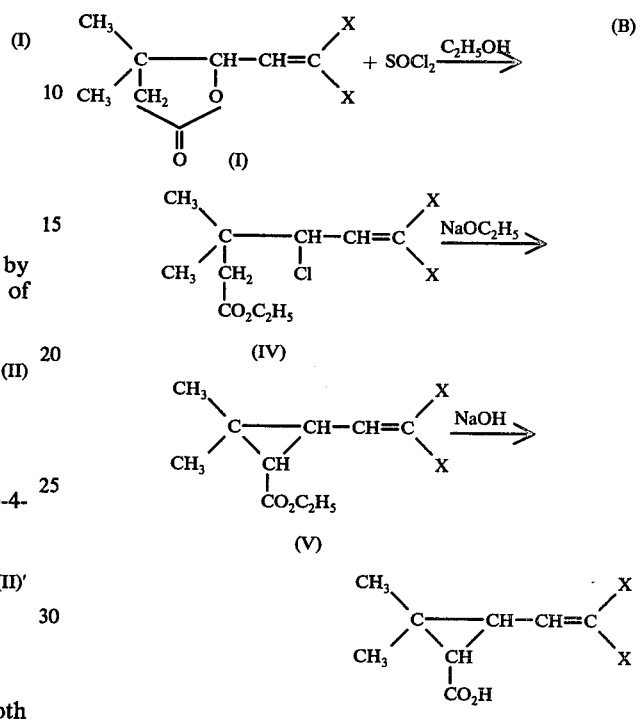

In this equation X is a halogen atom.

The cyclopropanecarboxylic acid of the formula (VI) is so far prepared, for example, by the method disclosed in Farkaš, et al., Chem. Listy, 52, 688–694 (1958). This process comprises many reaction stages and further it should use chemically very unstable and operationally very dangerous diazoacetic ester at the stage where the three-membered ring is formed. This process is not desirable even on a small scale synthesis in laboratories, and therefore it should be encountered by the more technical difficulties on a large scale industrial production.

At the present time the synthetic pyrethroid type compounds derived from the cyclopropanecarboxylic acid of the formula (VI) have been proved to have excellent usefulness, and so development of an easier and safer method for preparing such acid (VI) has been desired.

For the reasons described above, the present inventors studied a more advantageous synthetic method of the cyclopropanecarboxylic acid (VI). As the results, it has been found that the acid can be obtained from the same material as in Farkaš' method by the method of the present invention which has less reaction stages and is operationally safer and easier even on an industrial scale production than Farkaš' method. The process of the present invention is illustrated below.

For example, 1,1,1,-trichloro-4-methyl-3-pentene-2-ol of the formula (II)-a used in the present invention has a melting point of 81° to 82° C and 1,1,1-trichloro-4-methyl-4-pentene-2-ol of the formula (II)'-a has a melting point of about −20° C.

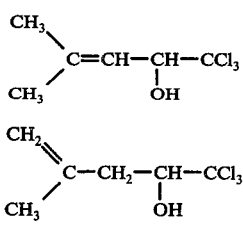

(II)-a (II)'-a

The both compounds are synthesized from chloral and isobutene by the foregoing Farkas' method or the method disclosed in Colonge, et al., Bull. soc. chim. France., 1957, 204–208.

The compounds (II)-a and (II)'-a are obtained by these methods as a mixture of the both and can be isolated from each other by the fractional crystallization, if necessary. It may also be possible to isomerize the mixture by heating in the presence or absence of Lewis acid into a system containing a larger proportion of the compound (II)-a.

As for the compounds which are easily derived from the compounds (II) and (II)' and are reversibly returned to the respective original compounds (II) and (II)' in the course of the reaction of the present invention, there are exemplified 1,1,1-trihalogeno-4-methylpentane-2,4-diol of the formula (II)″ and 1,1,1,4-tetrahalogeno-4-methyl-pentane-2-ol of the formula (II)‴. These derivatives are easily obtained by the addition of water and hydrogen halogenide, respectively, to the compound (II) or (II)'.

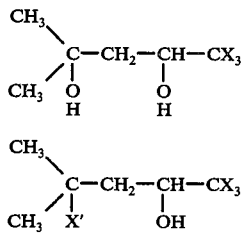

(II)″

(II)‴ wherein X and X' are a halogen atom respectively. For example, the compounds (II)″-a and (II)‴-a are prepared from the compounds (II)-a and (II)'-a respectively.

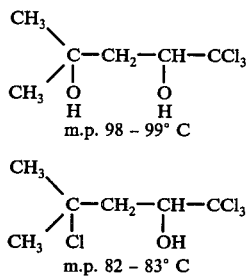

(II)″-a
m.p. 98 – 99° C (II)‴-a
m.p. 82 – 83° C

In carrying out the method of the present invention, the amount of sulfuric acid and the concentration of sulfuric acid are not particularly limited but, as to the latter, a relatively high concentration, for example more than 70%, is used.

The range of reaction temperature is preferably within a range from −30° C to room temperature. The reaction is completed in 30 minutes to 12 hours. The reaction may be carried out with addition of other Lewis acids such as boron trifluoride.

The reaction may be carried out by adding the alcohols of the formulae (II) and (II)' and the olefin of the formula (III) at the same time as a mixed solution, or by separately adding these three compounds. In contrast with this, sulfuric acid may be added to the mixed solution of the alcohols of the formulae (II) and (II)' and the olefin of the formula (III).

As a matter of course, all the compounds which are changeable to the compound (II) or (II)' in the reaction system are included in the scope of the present invention. The present reaction produces relatively large amounts of by-products but it is characterized in that the objective lactone of the formula (I) can be obtained by the simplest operation.

The present invention will be illustrated with reference to the following examples, but it is not intended to limit the present invention to these examples.

EXAMPLE 1

Five grams of water was added to 95 cc of conc. sulfuric acid and 33.2 g of boron trifluoride etherate was added dropwise thereto at about 5° C. To the resulting mixed solution was added dropwise a mixed solution of 20 g of 1,1,1-trichloro-4-methyl-4-pentene-2-ol and 14.5 g of vinylidene chloride at 6° to 7° C over 2 hours. Hydrogen chloride gas was generated during the addition. After the addition was completed, stirring was further continued at the same temperature for 2 hours. The reaction solution was poured into ice water, followed by extraction with hexane. After removing the hexane by distillation, the residue was distilled to separate 3.58 g of the fraction of 96°–100° C/20 mmHg. This fraction consisted essentially of 1,1,3,4-tetrachloro-4-methyl-1-pentene.

NMR $\delta_{TMS}^{CCl_4}$;
6.10 (1H, d, J = 10.0 Hz)
4.68 (1H, d, J = 10.0 Hz)
1.65 (6H, S)
IR $\nu_{max}^{neat}$ (cm$^{-1}$); 1608, 1450, 1105, 902

The distillation was further continued to separate 7.3 g of the fraction of 95°–120° C/0.5 mmHg. This fraction proved to contain a lactone from IR spectrum. This fraction was chromatographed over silica gel to separate 2.14 g of the objective 3,3-dimethyl-4-(2,2-dichlorovinyl)-4-hydroxybutyric-1,4-lactone (yield 10.4%).

NMR $\delta_{TMS}^{CCl_4}$;
6.00 (1H, d, J = 9.0 Hz)
4.88 (1H, d, J = 9.0 Hz)
2.40 (1H, d, J = 17.0 Hz)
2.30 (1H, d, J = 17.0 Hz)
1.25 (3H, S) 1.09 (3H, S)
IR $\nu_{max}^{neat}$ (cm$^{-1}$); 1790, 1613, 1460, 1290, 1160, 910

The chromatography was further continued to separate 0.63 g of 2-dichloromethylidene-4-methyl-3-hexenone.

NMR $\delta_{TMS}^{CCl_4}$;
6.30 (1H, m) 2.40 (4H, m)
2.08 (3H, S)
IR $\nu_{max}^{neat}$ (cm$^{-1}$); 1710, 1645, 1602, 890

On continuing the chromatography, 1.95 g of 4-methyl-5-(2,2-dichlorovinyl)-4-hydroxypentanoic-1,4-lactone was further obtained.

NMR $\delta_{TMS}^{CCl_4}$;
5.95 (1H, t, J = 7.0 Hz)
2.50 (4H, m) 2.05 (2H, m)
1.40 (3H, S)
IR $\nu_{max}^{neat}$ (cm$^{-1}$); 1775, 1610, 935

EXAMPLE 2

Six grams of water was added to 150 g of conc. sulfuric acid and cooled to −10° C. To the mixed solution was added a paste of 20 g of 1,1,1-trichloro-4-methyl-3-pentene-2-ol in 20 g of vinylidene chloride over about 20 minutes. The mixture was gradually returned to room temperature and stirred for 2 hours at room temperature. Thereafter, the procedure was carried out in the same manner as in Example 1 to obtain 4.9 g of the objective γ-lactone (yield 23.7%).

EXAMPLE 3

To a suspension of 20 g of 1,1,1-trichloro-4-methyl-3-pentene-2-ol in 41 g of vinylidene chloride was added dropwise a mixture of 300 g of conc. sulfuric acid and 12 g of water over about 30 minutes while stirring the suspension at about −5° C. The mixture was stirred overnight at the same temperature and poured into ice water, followed by extraction with n-hexane. After removing the n-hexane by distillation, a liquor comprising 8 g of sodium hydroxide, 28 g of water and 4 g of methanol was added to the resulting concentrated residue and the mixture was stirred at room temperature for 2 hours to carry out hydrolysis. After removing neutral substances by extraction with n-hexane, the hydrolyzed liquor was acidified with conc. hydrochloric acid. The precipitated oily substance was extracted several times with n-hexane and the combined extract was concentrated to obtain 8.0 g of a pale yellow oily substance. It was found by gas chromatography that this oily substance consisted of the objective γ-lactone and a lactone as a by-product in a ratio of 83 to 17. Consequently, the yield of the objective γ-lactone was 32.3%.

EXAMPLE 4

A mixed solution of 150 g of conc. sulfuric acid and 6 g of water was cooled to −10° C and to the solution was added dropwise a solution of 20 g of 1,1,1-trichloro-4-methyl-3-pentene-2-ol in 55 g of vinylidene chloride with stirring over about 30 minutes. After stirring the mixture at about −3° C for 5 hours, the mixture was treated in the same manner as in Example 3. The resulting pale yellow liquor was vacuum-distilled to obtain 10.0 g of the fraction of 85°–95° C/0.8 mmHg.

It was found by gas chromatography that this fraction consisted of the objective γ-lactone and a lactone as a by-product in a ratio of 85 to 15. Consequently, the yield of the objective lactone was 41.4%.

What we claim is:

1. A process for producing a 3,3-dimethyl-4-(2,2-dihalogenovinyl)-4-hydroxybutyric-1,4-lactone of the formula,

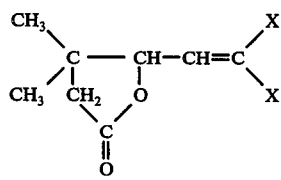

wherein X is a halogen atom which comprises reacting a 1,1,1-trihalogeno-4-methyl-3-pentene-2ol of the formula,

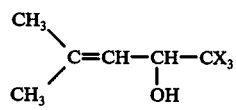

wherein X is a halogen atom, or a 1,1,1-trihalogeno-4-methyl-4-pentene-2-ol of the formula,

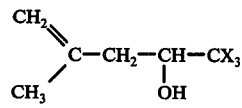

wherein X is a halogen atom, or the mixture of the both compounds with vinylidene chloride of the formula,

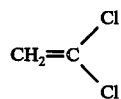

in sulfuric acid having a concentration of at least 70%.

2. A process according to claim 1, wherein X is a chlorine atom.

* * * * *